United States Patent [19]
Melvin

[11] Patent Number: 5,957,977
[45] Date of Patent: *Sep. 28, 1999

[54] ACTIVATION DEVICE FOR THE NATURAL HEART INCLUDING INTERNAL AND EXTERNAL SUPPORT STRUCTURES

[75] Inventor: David Boyd Melvin, Cincinnati, Ohio

[73] Assignee: University of Cincinnati, Cincinatti, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/581,914

[22] Filed: Jan. 2, 1996

[51] Int. Cl.$^6$ ............................... A61F 2/24; A61M 1/10; A61M 1/362; A61H 7/00
[52] U.S. Cl. ................................. 623/3; 623/2; 600/37; 600/16; 600/18; 601/153
[58] Field of Search ............................ 623/3, 2; 600/37, 600/16, 17, 18; 601/153

[56] References Cited

U.S. PATENT DOCUMENTS

| | | |
|---|---|---|
| 2,826,193 | 3/1958 | Vineberg . |
| 3,053,249 | 9/1962 | Smith . |
| 3,455,298 | 7/1969 | Anstadt . |
| 3,513,836 | 5/1970 | Sausse . |
| 3,590,815 | 7/1971 | Schiff . |
| 3,613,672 | 10/1971 | Schiff . |
| 3,668,708 | 6/1972 | Tindal . |
| 3,713,439 | 1/1973 | Cabezudo et al. . |
| 3,827,426 | 8/1974 | Page et al. . |
| 3,983,863 | 10/1976 | Janke et al. ................................. 623/2 |
| 4,192,293 | 3/1980 | Asrican . |
| 4,536,893 | 8/1985 | Parravicini . |
| 4,621,617 | 11/1986 | Sharma . |
| 4,690,134 | 9/1987 | Snyders . |
| 4,846,831 | 7/1989 | Skillin ......................................... 623/3 |
| 4,904,255 | 2/1990 | Chareire et al. ............................ 623/3 |
| 5,109,843 | 5/1992 | Melvin et al. ............................... 623/3 |
| 5,119,804 | 6/1992 | Anstadt . |
| 5,131,905 | 7/1992 | Grooters . |
| 5,139,517 | 8/1992 | Corral ......................................... 623/3 |
| 5,201,880 | 4/1993 | Wright et al. ............................... 623/2 |
| 5,256,132 | 10/1993 | Snyders . |
| 5,258,021 | 11/1993 | Duran ......................................... 623/2 |
| 5,334,217 | 8/1994 | Das ......................................... 606/213 |
| 5,358,519 | 10/1994 | Grandjean ................................... 623/3 |
| 5,370,685 | 12/1994 | Stevens ....................................... 623/2 |
| 5,383,840 | 1/1995 | Heilman et al. . |
| 5,487,760 | 1/1996 | Villafana ..................................... 623/3 |
| 5,533,958 | 7/1996 | Wilk ......................................... 600/18 |
| 5,713,954 | 2/1998 | Rosenberg et al. . |

FOREIGN PATENT DOCUMENTS

| | | | |
|---|---|---|---|
| 0119357 | 9/1984 | European Pat. Off. . | |
| 1191-076 | 11/1985 | U.S.S.R. ..................................... | 623/2 |

*Primary Examiner*—Michael J. Milano
*Assistant Examiner*—Tram A. Nguyen
*Attorney, Agent, or Firm*—Dinsmore & Shohl LLP

[57] ABSTRACT

An activator device for activation of cardiac tissue having a stint for placement within the interior volume of a natural heart adjacent cardiac tissue thereof. The device also includes a yoke for placement around a portion of the exterior surface of the natural heart in general alignment with the stint and connected to the stint by at least one cord. The device provides a simple yet reliable mechanism for assisting in extended activation of a natural heart with minimal impact and intrusion.

26 Claims, 4 Drawing Sheets

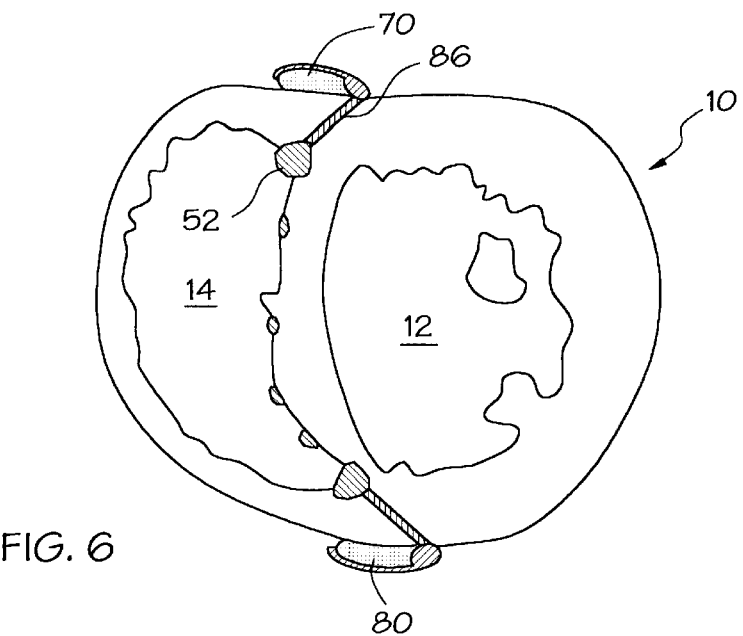
FIG. 6
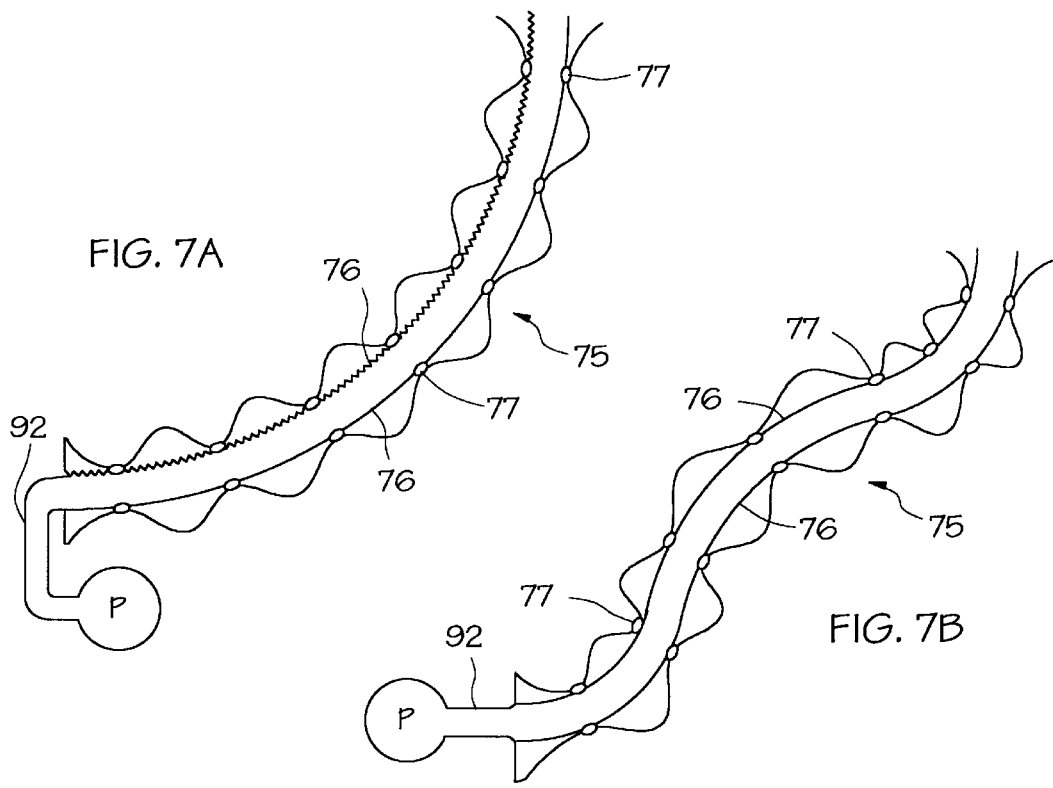
FIG. 7A
FIG. 7B

ACTIVATION DEVICE FOR THE NATURAL HEART INCLUDING INTERNAL AND EXTERNAL SUPPORT STRUCTURES

TECHNICAL FIELD OF THE INVENTION

The present invention relates to a device and method for assisting in the activation and operation of a living heart, and more specifically, for mechanically deforming cardiac tissue such that the circulation of blood is maintained.

BACKGROUND OF THE INVENTION

The natural heart, and specifically, the cardiac tissue of the natural heart can fail for various reasons to a point where the natural heart cannot provide sufficient circulation of blood for a body so that life can be maintained. As a solution for the failing natural heart, several attempts have been made in the past to provide a device to maintain circulation.

One such approach has been to either assist or to entirely replace the existing natural heart in a patient with an artificial heart, or to transplant a natural heart from another human into a patient. Several drawbacks have limited use of these devices and transplants to applications of a brief time period. As such, these devices and transplants have a real lasting benefit and use to only a tiny fraction of those afflicted with a failing natural heart.

A particular problem stems from the fact that the materials used for the interior lining of the chambers of an artificial heart are in direct contact with the circulating blood, which can enhance undesirable clotting of the blood, build up of calcium, or otherwise inhibit the blood's normal function. Hence, thromboembolism and hemolysis could occur with greater ease. Additionally, an artificial heart lining can crack, which inhibits performance, even if the crack is at a microscopic level.

The transplant procedure requires removing an existing organ (i.e., the natural heart) for substitution with another organ (i.e., another natural heart) from another human, or potentially, from an animal. Before replacing an existing organ with another, the substitute organ must be "matched" to the recipient, which can be, at best, difficult and time consuming to accomplish. Furthermore, even if the transplanted organ matches the recipient, a risk exists that the recipient's body will reject the transplanted organ and attack it as a foreign object. Moreover, the number of potential donor hearts is far less than the number of patients in need of a transplant. Although use of animal hearts would lessen the problem with fewer donors than recipients, there is an enhanced concern with rejection of the animal heart.

In an effort to use the existing natural heart of a patient, other attempts have been made to wrap skeletal muscle tissue around the natural heart to use as an auxiliary contraction mechanism to pump the natural heart. As currently used, skeletal muscle cannot alone typically provide sufficient and sustained pumping power for maintaining circulation of blood through the circulatory system of the body, especially for those patients with severe heart failure.

Still another concept for maintaining the existing natural heart as the pumping device involves enveloping a substantial portion of the natural heart, such as the entire left and right ventricles, with a pumping device for rhythmic compression. Although somewhat effective as a short term treatment, the pumping device has not been suitable for long term use. Typically, a vacuum pressure is needed to overcome cardiac tissue/wall stiffness so that the chambers can return to their original volume and refill with blood. This "active filling" of the chambers with blood limits the ability of the pumping device to respond to the need for adjustments in the blood volume pumped through the natural heart, and can adversely affect the circulation of blood to the coronary arteries. Natural heart valves are quite sensitive to wall and annular distortion, and movement patterns that reduce a chamber's volume do not necessarily facilitate valve closure (which can lead to valve leakage). Another major obstacle with long term use of such pumping devices is the deleterious effect of extensive mechanical contacting of living internal surfaces (endocardium). In certain cases, this coaptation of endocardium tissue is probably mechanically necessary for a device that encompasses both ventricles to produce independent output pressures, but it can compromise the integrity of the living endothelium.

Another device developed for use with an existing heart for sustaining the circulatory function of a living being and the pumping action of the natural heart is an external bypass system, such as a cardiopulmonary (heart-lung) machine. Typically, bypass devices of this type are complex and large, and, as such, are limited to short term use in an operating room during surgery, or to maintaining the circulation of a patient while awaiting receipt of a transplant heart. The size and complexity effectively prohibit use of bypass systems as a long term solution, as they are rarely even portable devices. Furthermore, long term use of a heart lung machine can damage the blood cells and blood borne products, resulting in post surgical complications such as bleeding, thromboembolism function, and increased risk of infection.

Consequently, none of the previous available techniques or devices for maintaining circulation of blood provided an adequate or practical long-term use device or technique for adequately maintaining sufficient blood pressure and circulation of blood through the circulatory system of the body.

SUMMARY OF THE PRESENT INVENTION

It is the object of the present invention to provide a device and method for activation of a natural heart that provides different independent pressures to the left and right side of the natural heart.

It is another object of the present invention to provide a device and method for activation of a natural heart that minimizes damage to the coronary circulatory and the endocardium (lining tissue).

It is still a further another object of the present invention to provide a device and method for activation of a natural heart that allows one or more of the heart chambers to rapidly and passively refill at low pressure after an activation stroke.

Another object of the present invention is to provide a device and method for the activation of a natural heart that supports and maintains competence of the heart valves so the heart valves can function as designed.

Still another object of the present invention is to provide a device and method for the activation of the heart that functions at the proper rate.

Yet another object of the present invention is to provide an apparatus and method for the activation of a natural heart on a long term basis.

It is yet still an object of the present invention to provide a device and method for the activation of a natural heart to provide an implant device that does not require removal of an existing natural heart.

Additional objects, advantages, and other features of the present invention will be set forth and will become apparent to those skilled in the art upon examination of the following, or may be learned with practice of the invention.

To achieve the foregoing and other objects, and in accordance with the purpose herein, the present invention comprises an activator device for use with a natural heart having an internal stint for placement within the interior volume of a natural heart adjacent cardiac tissue. The device also includes a yoke for placement around a portion of the exterior surface of the natural heart in general alignment with the stint and is connected to the stint by at least one cord.

Preferably, the activator device includes a first ring for placement around at least one of the atrioventricular valve annuli, a second ring for placement around at least one of the outflow valve or semilunar annuli, and a septal splint having a frame and sutures in a net-like configuration to stabilize the septal wall between chambers of the natural heart. The first ring, second ring, and the septal splint are connected to each other using fastening elements.

In a preferred embodiment, the yoke is sized and configured for placement adjacent at least a portion of the interventricular groove, preferably adjacent at least a portion of the anterior and posterior portions of the interventricular groove, and more preferably adjacent at least a substantial portion of the anterior and posterior portions of the interventricular groove. In another embodiment, the yoke is sized and configured for placement adjacent at least a portion of the atrioventricular groove.

The present invention also includes an activator attached to the yoke for deforming the natural heart, which preferably includes a hydraulic lateral arm.

The present invention also includes a method for cardiac tissue deformation using the above-described device. The activator deforms a portion of the cardiac tissue by moving an arm from a relaxed condition to an activated condition. As the activator is pressing against the natural heart, the volume of at least one chamber of the natural heart, is decreased so that blood is pumped out of the natural heart and into the circulatory system. Thereafter, the activator releases from against a portion of the cardiac tissue returns to the relaxed condition. The combination of the stint and yoke assist in returning the volume of the chamber so that at least one of the chambers of the natural heart refills with blood and thus, the steps can be repeated.

Different forces can be applied to a natural heart for reducing the volume of at least one of the chambers. These forces can include applying a torsion force or a shearing to the natural heart, flattening a portion of the cardiac tissue, applying a uniform pressure to the natural heart, and/or applying an indentation against at least one point on the exterior wall of the natural heart.

BRIEF DESCRIPTION OF THE DRAWINGS

While the specification concludes with claims particularly pointing out and distinctly claiming the present invention, it is believed the same will be better understood from the following description taken in conjunction with the accompanied drawings in which:

FIG. 6 is a top sectional schematic view of a natural heart with an internal splint and an external yoke of the present invention illustrated being connected by transmural cords;

FIG. 7A is a partial schematic view of an exemplary activator of the present invention in a relaxed condition; and FIG. 7B is a partial schematic view of an exemplary activator of the present invention in an activated condition.

DETAILED DESCRIPTION OF THE PREFERRED EMBODIMENT

Figure 1:
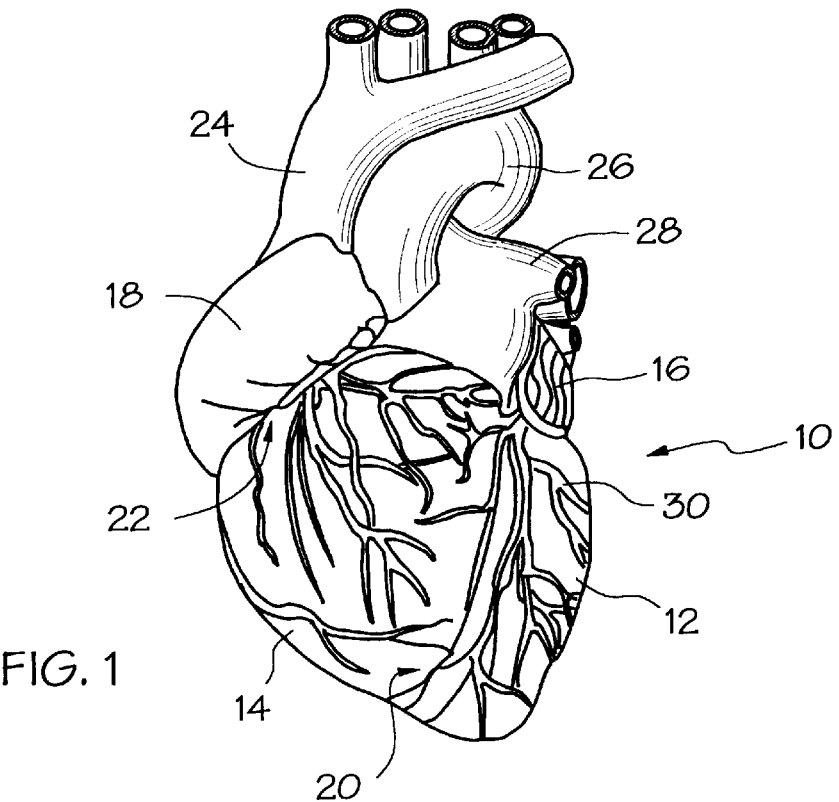
FIG. 1 is a partial frontal anterior perspective view of an exemplary natural heart.

Referring now to the figures in detail wherein like numerals indicate the same elements throughout the views, a natural heart, generally indicated in FIG. 1 as 10, has a lower portion comprising two chambers, namely a left ventricle 12 and a right ventricle 14, which function primarily to supply the main force that propels blood through the circulatory system. A natural heart 10 also includes an upper portion having two chambers, a left atrium 16 and a right atrium 18, which primarily serve as an entryway to the ventricles 12 or 14, and assist in moving blood into the ventricles 12 or 14. The interventricular wall of cardiac tissue separating the left and right ventricles 12 or 14, respectively, is defined by an interventricular groove 20 on the exterior wall of the natural heart 10. The anterioventricular wall of cardiac tissue separating the lower ventricular region from the upper atrium region is defined by anterioventricular groove 22 on the exterior wall of the natural heart 10.

Generally, the ventricles are in fluid communication with the atria through an atrioventricular valve. More specifically, the left ventricle 12 is in fluid communication with the left atrium 16 through the mitral valve, while the right ventricle 14 is in fluid communication with the right atrium 18 through the tricuspid valve. Generally, the ventricles are in fluid communication with the circulatory system (i.e., the pulmonary and peripheral circulatory system) through semilunar valves. More specifically, the left ventricle 12 is in fluid communication with the aorta 26 of the peripheral circulatory system, through the aortic valve, while the right ventricle 14 is in fluid communication with the pulmonary artery 28 of the pulmonary, circulatory system through the pulmonic valve.

Figure 2:
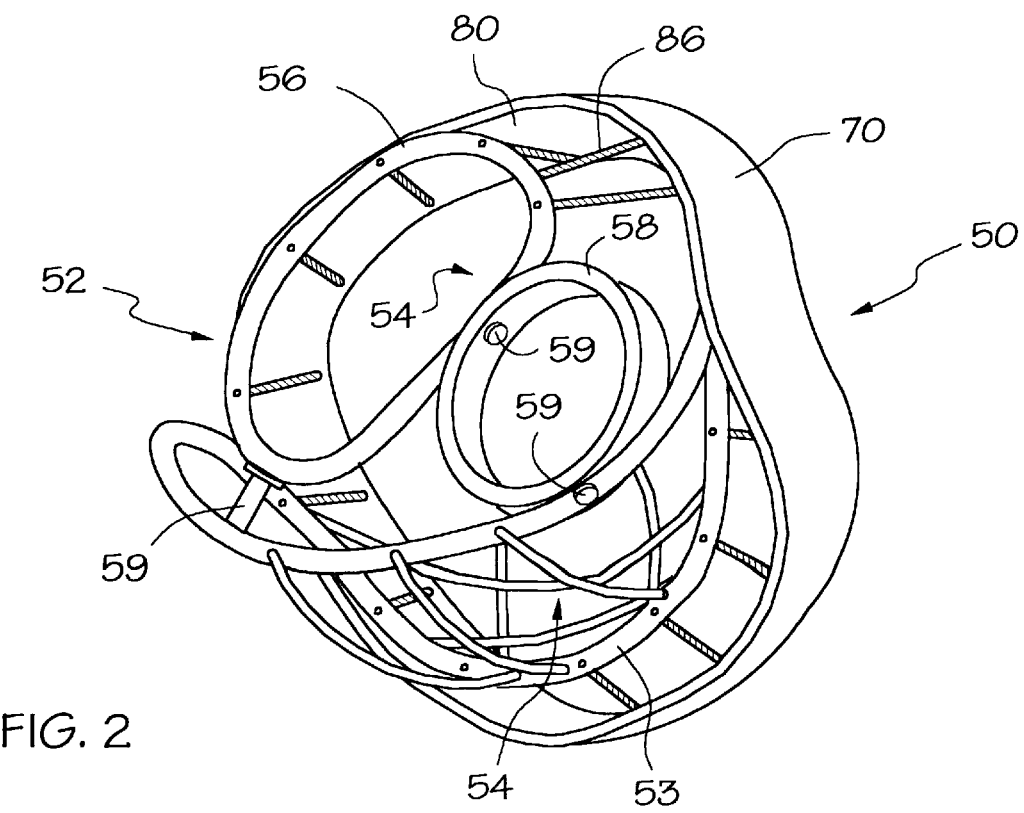
FIG. 2 is a perspective view of an internal stint and exterior yoke made in accordance with the present invention.

By way of a non-limiting example, the present invention will be discussed in terms of embodiments that are used to primarily assist in the activation and operation of the left ventricular portion of the natural heart 10, however, it is noted that the present invention can also be used to assist in the activation and operation of other portions of the natural heart 10, such as the atria, or the right ventricular portion of the natural heart 10. The present invention is a mechanical activator, illustrated in FIG. 2 as 50, which includes an internal stint 52. Furthermore, the present invention includes an external yoke 70 fixed to the internal stint 52 by transmural cords 86. The internal stint 52 is sized and configured for placement within the interior volume of the natural heart 10, and includes a generally triangular shaped frame 53 that can be assembled from a plurality of interlocking struts, preferably an anterior strut 62, a posterior strut 63, and a basal strut 64. The stint 52 also includes at least two separate ring structures, namely a first ring 56 sized and configured for placement adjacent the atrioventricular valve annuli, and preferably suprajacent the mitral valve annuli in the left atrium 16, and a second ring 58 sized and configured for placement adjacent the semilunar valve annuli preferably subjacent the aortic valve annuli in the left ventricle 12.

Figure 3:
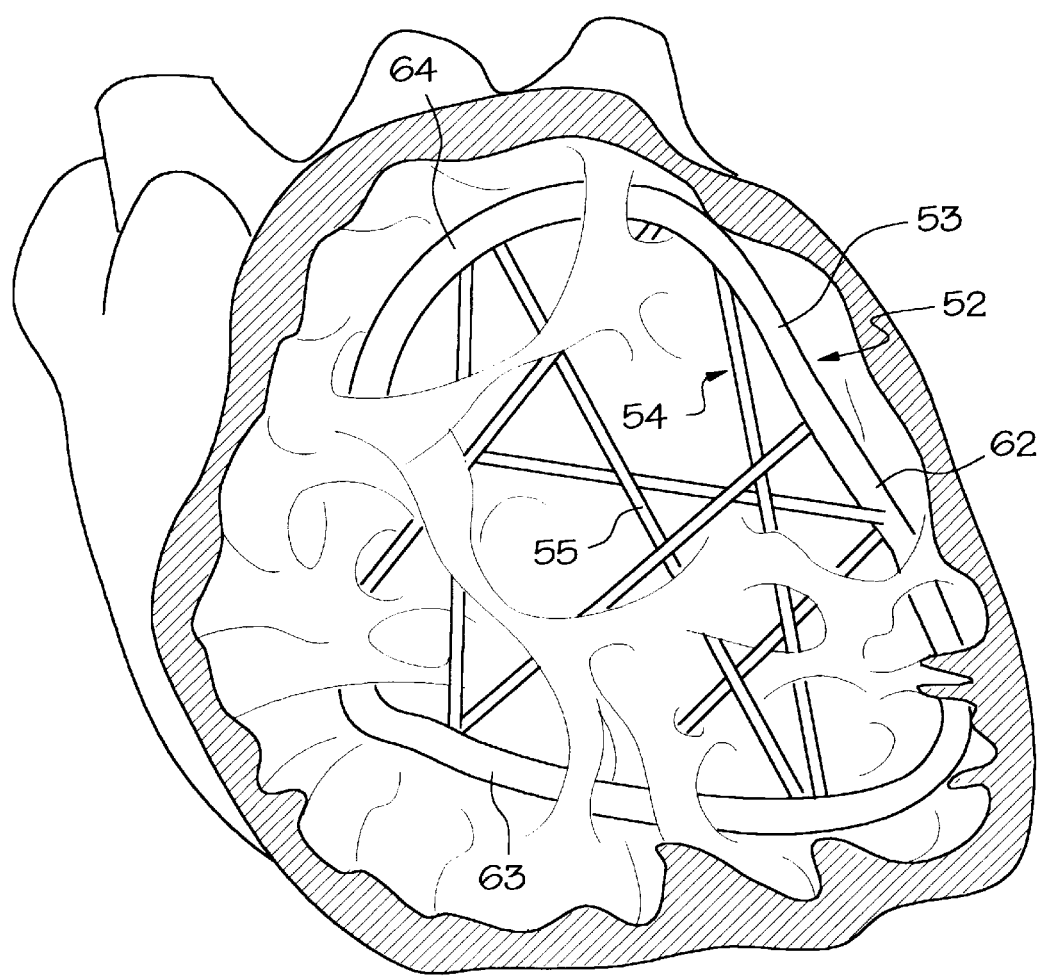
FIG. 3 is a partial cross-sectional view of a natural heart with a septal splint made in accordance with the present invention placed within a natural heart.

FIG. 3 further illustrates a septal splint 54, which can include one or more strands of sutures (e.g., 55) affixed to the frame 53 through loops positioned on the frame 53, preferably the loops are affixed to the inner portion of frame 53, and more preferably, at about 1.5 cm intervals. The splint 54 can take the form of a tennis racket-like shaped configuration or a snowshoe like shaped configuration to brace or stabilize one side of the septum, preferably the right side of the interventricular septum without distortion of the chordae. Preferably, the septal splint 54 is positioned by stringing a heavy monofilament polypropylene suture, such as a #5 polypropylene suture, under, through, and behind the trabeculae, and through the loops as will be discussed later in great detail. The first and second rings 56 and 58 and the septal splint 54 are attached at least to each other using connectors 59, such as a pin to assist in maintaining the relative position so that the first and second rings 56 and 58, respectively, and the splint 54 are supported while the natural heart 10 is being activated.

So that the components of the stint 52 (e.g., the septal splint 54 and first and second rings 56 and 58) are not totally rigid and can exhibit an elastic quality, the components are preferably made of a stiff coil spring material covered with braided polyester. Localized adjustments can be made to the elasticity of the various components of the stint 52 to reduce the potential for problems, such as damaging the cardiac tissue or compromising the coronary circulation.

Figure 4:
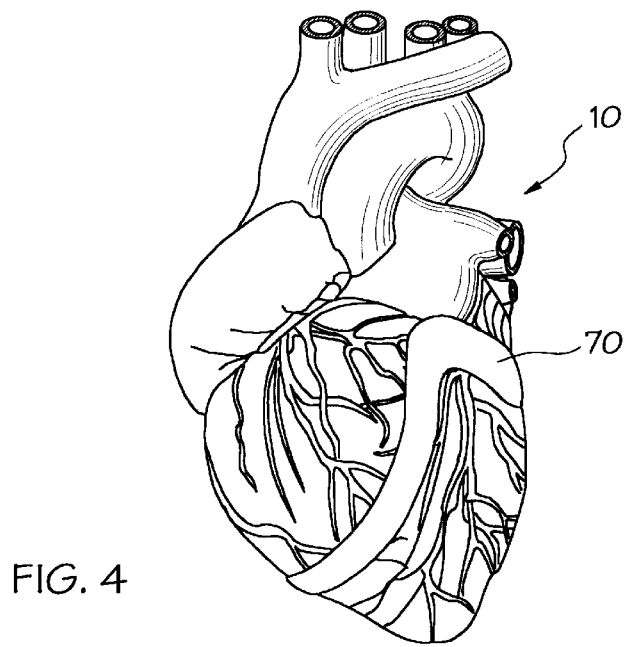
FIG. 4 is a partial frontal perspective view of a natural heart with an external yoke placed on a natural heart.

As illustrated in FIG. 4, the device 50 also includes an external yoke 70 for placement around a portion of the exterior surface of a natural heart 10. The generally stirrup shaped yoke 70 restricts free motion of the natural heart 10 so that the natural heart 10 can be activated. Preferably, the yoke 70 is between about 1 and 2 cm wide and includes a semi-rigid collar portion, preferably made of polypropylene, for providing rigidity to the yoke 70. Additionally, the yoke 70 can include a gel-filled cushion portion 80 that is positioned immediately adjacent exterior surface of the natural heart 10 for providing equalized pressure over the irregularities in the epicardial surface of the natural heart 10, and preferably, any of the coronary arteries 30 within each region under the yoke 70. Preferably, the yoke 70 is sized and configured for placement adjacent at least a portion of the atrioventricular groove 22, more preferably, at least a portion of the anterior and posterior portions of the interventricular groove 20, and most preferably, at least a substantial portion of the anterior and posterior portion of the interventricular groove. In yet another embodiment, the yoke 70 is sized and configured for placement adjacent at least a portion of the atrioventricular groove 22.

Referring now to FIG. 6, general alignment of the yoke 70 is maintained by at least one transmural cord 86, and preferably, a plurality of cords 86 that penetrate the walls of the natural heart 10 and connect to the stint 52. The cord 86 is preferably made of a heavy braided, polymer-impregnated polyester suture core (such as #5 Ethiband® by Ethicon, Inc.) covered in the intermyocardial portion with a braided sleeve of polyester yarn to promote firm tissue growth around the cord 86. When it is necessary to utilize more than one cord 86 with the present invention, spacing of the cords 86 should preferably be at intervals of between about 15 mm to 20 mm along the yoke 70, from the septal splint 54 and the first ring 56 extending obliquely outwardly toward the left ventricle exterior wall for insertion into the left ventricle margin of the yoke 70. More preferably, the cords 86 should be positioned for avoiding contact with the coronary vessels 30. The cords 86 vary in length such that the splint 54 and first ring 56 are oriented beneath the gel-filled cushion portion while the septum stint 52 and the first ring 56 are held stable in general alignment with the natural heart 10, and are generally not allowed to move away from the ventricular exterior wall when pressure is applied to a natural heart 10 via by activator 74.

Figures 5A, 5B:
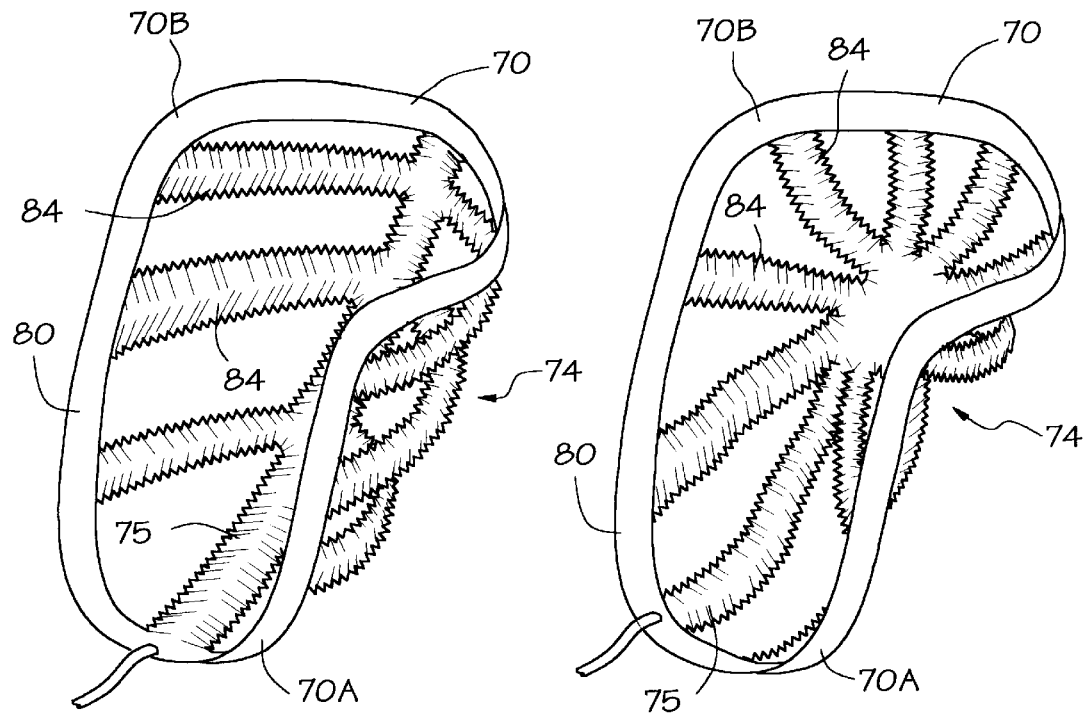
FIG. 5A is a frontal perspective view of one embodiment of the external yoke and activator of the present invention.
FIG. 5B is a frontal perspective view of another embodiment of an external yoke and activator of the present invention.

As mentioned above, the present invention also includes an activator 74 attached to at least a portion of the yoke 70, preferably the apical portion 70a, as illustrated in FIGS. 5A and 5B. The activator 74 includes a lateral flexible arm 75 generally having an "L" shaped configuration that extends approximately two-thirds of the distance between the apical portion 70a and base portion 70b of the yoke 70.

Connected to the arm 75 is at least one, and preferably a plurality of, bands 84 extending away from the arm 75 sized and configured for placement adjacent the exterior surface of the natural heart 10. The distal ends of the bands 84 are typically affixed and secured along portions of yoke 70.

One embodiment of the yoke 70 and activator 74 is illustrated in FIG. 5A in which the bands 84 extend perpendicularly away from the arm 75 and connect to the anterior and posterior portions of yoke 70. In another embodiment of the yoke 70 and activator 74 as illustrated in FIG. 5B, bands 84 extend radially away from the distal end of the arm 75.

Referring now to FIGS. 7A and 7B, the activator 74 preferably has a hydraulic lateral arm 75 having a tubed-shape corrugated configuration with rings 77 affixed to the inner aspect of each corrugation. A plurality of longitudinally extending cords 76, preferably three or more, are affixed to the inner portion of arm 75, preferably the distal end of arm 75 and also to each of, preferably, each of the rings 77. The cords 76 can vary in length, especially between the fixation points to each ring 77 for controlling the separation distance between rings 77. In fluid communication with the arm 75 via a driveline 92 is a pump unit "P", such as pneumatic or a hydraulic pump for controlling or altering the fluid volume within the arm 75.

FIG. 7A illustrates the arm 75 in a relaxed condition when fluid pressure within arm 75 is at or below ambient levels and where the shape of arm 75 is determined by the external forces and the intrinsic stiffness of arm 75. To utilize the present invention, pressure within the arm 75 can be increased, preferably above ambient levels, so that the shape of the arm 75 is altered to an activated condition, as illustrated in FIG. 7B. The length difference of the various cords 76 between the rings 77 controls the radius of curvature of the arm 75 and the direction of curvature at various portions along the longitudinal length of the arm 75. The amount of pressure required within the arm 75 must be sufficient to overcome the intrinsic stiffness of the arm 75 at ambient condition, and to facilitate the proper deformation of both the arm 75 and bands 84 so that the proper amount of pressure is applied to the exterior wall of the natural heart 10 to assist in altering (i.e., reducing) the volume of one or more chamber of a natural heart 10 (e.g., the left ventricle 12) to maintain circulation of the blood through the circulatory system.

In a preferred embodiment, the arm 75 can be customized to apply different pressure to different portions of the natural heart 10. For example, varying the diameter of arm 75 along the longitudinal length can assist in controlling the curvature of arm 75. Regions of the arm 75 needing less bending moment can have a smaller diameter and regions of the arm 75 where greater bending moments are preferred can have a larger diameter.

Various embodiments of an activator 74 can be utilized with the present invention to achieve a change in the volume of one or more heart chambers. It is noted that any activator 74 used with the present invention should be sufficient so that the cardiac output of a typical adult is between about 3 l/min and about 30 l/min, and preferably between about 5 l/min and 20 l/min.

In addition, there are various possible forces which can be used for activating and thus, altering the chamber volumes of the natural heart 10. The present invention can be utilized to flatten the exterior wall of the natural heart 10 in a plane substantially perpendicular to the plane of the atrioventricular valves (e.g., a mitral valve) or substantially parallel to the septum. When utilizing such a force, the activator 74 should be configured to produce a flexion in the convex direction limited to between about 2.5 to 3.0 times the curvature value of the exterior wall of the natural heart 10 during the diastolic portion of the cardiac cycle. Deflection in a concave direction is restricted only to those bands 84 extending away from the arm 75 and connecting to the base portion 70b of yoke 70.

Also, an activator 74 can be used to apply a uniform pressure to substantially the entire exterior wall of the natural heart 10.

Furthermore, the activator 74 can be used to indent the exterior wall of the natural heart 10 at more than one location, and preferably at two or three locations on either an exterior wall or the septum in a hemispheric or hemiellipsoid profile.

Additionally, an activator 74 can apply a torsion force to at least a part of the natural heart 10 at various angles.

In yet another embodiment, the activator 74 can apply a shearing force to a portion of the lateral exterior wall, which is directed apically and is a basal sheer force applied on the right side of the stint 52.

When the orientation of the arm 75 is altered from the relaxed condition, which is illustrated in FIG. 7A, to the activated condition, which is illustrated in FIG. 7B, the arm 75 and the bands 84 deform and apply pressure against the exterior wall of the natural heart 10 for assisting with or facilitating activation of the natural heart 10 (the systolic portion of the cardiac cycle). As a result, the volume of one or more chambers of the natural heart 10 is reduced and blood is pumped out of the natural heart 10 and into the circulatory system.

Following the activation (i.e., systolic portion of the cardiac cycle), the arm 75 and bands 84 release from against the cardiac tissue and return to their relaxed condition. The combination of the stint 52 and the yoke 70 assists in returning the deformed portion of the natural heart 10 back to its pre-activation volume so that it can refill with blood during the diastolic portion of the cardiac cycle, so that the entire cardiac cycle can be repeated.

To position the device 50 into and around an existing natural heart 10, open heart thoracic surgery is required. Clinically, sufficient anesthesia is administered to the patient and the thoracic cavity is opened using standard thoracic procedures.

Once the thoracic cavity is opened, circulation of blood to the natural heart 10 must be bypassed so the present invention can be inserted into the patient. Referring initially to FIG. 1, the superior vena cava 24, the inferior vena cava (not shown), and aorta is 26 are cannulated. The circulatory system is connected to a cardiopulmonary bypass machine so that circulation and oxidation of the blood are maintained during the procedure. By way of example, the procedure discussed in detail will be for insertion of the present invention to assist in the activation and operation of the left ventricle 12.

Through an aortotomy and an interatrial groove left atriotomy, the first and second rings 56 and 58, respectively, are inserted and sutured in position. Preferably, the first ring 56 is positioned suprajacent the mitral annuli and the second ring 58 is positioned subjacent the aortic annuli.

The interlocking struts of the septal frame 53 (e.g., anterior, strut 62, a posterior strut 63, and a basal strut 64) are inserted into the right ventricle 14 through an apical ventriculotomy, a right atriotomy with partial temporary detachment of the septal tricuspid leaflet of the tricuspid valve, and an outflow tract ventriculotomy, respectively. Suture 55 strands are then passed back and forth against the interventricular septum, threading through loops to provide a septal splint 54. In placement of both the various struts of frame 53 and the strands 55 that form splint 54, care is taken to maneuver behind chordae and behind or through major trabeculae and bases of papillary muscles. The suture strands 55 are tied to form the net-like configuration of the septal splint 54 that lies snugly against the septum, but allows it to maintain normal rightward convexity. Separate connector elements 59, preferably pins, are placed to joint the first ring 56 and the second ring 58, the second ring 58 and the septal splint 54, and the septal splint 54 and the first ring 56.

Next, the left pleural cavity is opened and the yoke 70 is positioned behind the natural heart 10. Cords 86 are assembled as 12" strands of suture with a polyester bead fused to one end and blunt straight needle on the other. Each suture is passed through a hole in the margin of the yoke 70, through the cardiac tissue, and preferably the ventricular wall, and through the internal stint 52 (i.e., first ring 56 or septal splint 54) and anchored after length adjustment, with the excess portion of the sutures cut and removed. Cords 86 are tightened to render the intrinsically flexible stint 52 relatively taut and control bulging, preferably in a rightwardly direction.

Cardiotomies are closed, and the activator 74 is attached to the yoke 70. The driveline 92 is attached to the drive unit "P" and all indicated monitoring lines are positioned. Preferably, Heparin-filled Teflon-coated polyurethane 5 Fr. catheters are brought through the posterior cervical incision into the chest and into the atrial appendages and an identical one into a branch of the innominate artery. Termination of a cardiopulmonary bypass is attempted and, if successful, the thoracotomy is closed.

An alternative method for positioning the present invention includes removing the natural heart 10 from the patient, positioning all the components of the present invention, as discussed above, and auto-transplanting the natural heart 10 back into the patient using standard cardiectomy and cardiac transplant techniques known in the industry.

Having shown and described the preferred embodiments to the present invention, further adaptations of the activation device for the living heart and method of deforming the living heart as described herein can be accomplished by appropriate modifications by one of ordinary skill in the art without departing from the scope of the present invention. For example, the present invention can be used with any one or even a plurality of the various chambers of a living heart, and also could be used with different activators 74. Other examples of an activator 74 usable with the present invention include a girdle assembly that can be activated by hydraulics forces or other forces, such as an electromagnetic for using magnets and electrical current. Several such potential modifications have been discussed and others will be apparent to those skilled in the art. Accordingly, the scope of the present invention should be considered in terms of the following claims and is understood not to be limited in the details, structure and operation shown and described in its specification and drawings.

I claim:

1. A mechanical ventricular activation device for use with a natural heart, said device comprising:
    (a) a stint for placement within the interior volume of a natural heart adjacent cardiac tissue thereof, said stint configured for supporting at least a portion of the internal tissue of the natural heart;
    (b) a yoke for placement around a portion of the exterior surface of the natural heart in general alignment with said stint;
    (c) at least one cord connecting said stint and said yoke; and
    (d) an activator attached to said yoke for providing cyclically alternating forces.

2. A device for use with a natural heart for placement within the interior portion of the natural heart thereof, comprising:
    a substantially perforate septal splint configured for allowing blood flow therethrough and for stabilizing at least a portion of the internal tissue of the natural heart, the septal splint having a frame with an opening; and a plurality of suture strands extending transverse the opening of said frame, wherein the plurality of suture strands is configured to be positioned in contact with at least a portion of the internal tissue of the heart.

3. The device of claim 2, wherein said frame comprises a plurality of interlocking struts connected to each other.

4. The device of claim 2, wherein said device comprises a ring for placement adjacent one of the annuli of the natural heart and a connector of an artificial material for joining said ring and said septal splint.

5. The device of claim 4, wherein said device comprises:
    a first ring configured for placement adjacent one of the annuli of the natural heart;
    a second ring for placement adjacent another of the annuli of the natural heart; and
    a connector of artificial material for joining said first ring and said second ring.

6. The device of claim 2, wherein said septal splint comprises a tennis racket-like shaped configuration.

7. The device of claim 2, wherein said septal splint comprises a stiff rail spring material covered with a braided polyester.

8. The device of claim 2, wherein said suture strands comprise a heavy monofilament polypropylene suture.

9. The device of claim 2, wherein said suture strands comprise a network of filaments configured to be positioned adjacent at least a portion of the septal wall.

10. The activation device of claim 2, further comprising:
    (a) a yoke for placement around a portion of the exterior surface of the natural heart in general alignment with said splint; and
    (b) at least one cord connecting said splint to said yoke.

11. The activation device of claim 10, wherein said yoke is sized and configured for placement adjacent at least a portion of an atrioventricular groove of the natural heart.

12. The activation device of claim 10, wherein said yoke is sized and configured for placement adjacent at least a portion of an interventricular groove of the natural heart.

13. The activation device of claim 12, wherein said yoke is sized and configured for placement adjacent at least a portion of the anterior and posterior portions of said interventricular groove.

14. The device of claim 2, wherein the plurality of suture strands is configured to be positioned against at least a portion of the internal tissue of the heart.

15. The device of claim 2, wherein the plurality of suture strands is configured to be positioned inserted into at least a portion of the internal tissue of the heart.

16. The devices of claim 2, wherein the plurality of suture strands comprises a wire.

17. A device for use with a natural heart for placement within the interior portion of the natural heart adjacent cardiac tissue thereof, comprising:
    a first ring configured for placement adjacent one of the annuli of the natural heart;
    a second ring for placement adjacent another of the annuli of the natural heart; and
    a connector of artificial material joining said first ring and said second ring configured for extending through said tissue of said heart.

18. The device of claim 17, wherein said first ring can be configured for placement adjacent an atrioventricular valve of the natural heart.

19. The device of claim 17, wherein said first ring can be configured for placement adjacent a semilunar valve of the natural heart.

20. The device of claim 17, wherein said device comprises a septal splint configured for stabilizing at least a portion of a septal wall of the natural heart, and a second connector for joining one of the rings and said septal splint.

21. The device of claim 20, wherein said second connector comprises separate connectors for joining said first ring and said septal splint; and for joining said second ring and said septal splint.

22. The device of claim 17, wherein said connector comprises a pin.

23. A mechanical ventricular activation device for use with a natural heart, said device comprising:
    (a) a stint for placement within the interior volume of a natural heart adjacent cardiac tissue thereof;
    (b) a yoke for placement around a portion of the exterior surface of the natural heart in general alignment with said stint;
    (c) at least one cord connecting said stint to said yoke; and
    (d) an activator attached to said yoke, said activator comprising an arm having a distal end and a plurality of bands connected to said arm.

24. The device of claim 23, wherein said plurality of bands extend away from said arm.

25. The device of claim 23, wherein said plurality of bands extend radially away from the distal end of said arm.

26. The device of claim 23, wherein said plurality of bands extend perpendicularly away from the distal end of said arm.

* * * * *